United States Patent
Wright

(10) Patent No.: US 9,446,049 B2
(45) Date of Patent: Sep. 20, 2016

(54) HORMONE REPLACEMENT FORMULATION

(76) Inventor: Jonathan V. Wright, Auburn, WA (US)

( * ) Notice: Subject to any disclaimer, the term of this patent is extended or adjusted under 35 U.S.C. 154(b) by 459 days.

(21) Appl. No.: 11/371,580

(22) Filed: Mar. 9, 2006

(65) Prior Publication Data

US 2007/0212427 A1   Sep. 13, 2007

(51) Int. Cl.
| | | |
|---|---|---|
| *A61K 31/56* | (2006.01) | |
| *A61K 31/202* | (2006.01) | |
| *A61K 31/405* | (2006.01) | |
| *A61K 31/4415* | (2006.01) | |
| *A61K 31/57* | (2006.01) | |
| *A61K 33/04* | (2006.01) | |

(52) U.S. Cl.
CPC ............ *A61K 31/56* (2013.01); *A61K 31/202* (2013.01); *A61K 31/405* (2013.01); *A61K 31/4415* (2013.01); *A61K 31/57* (2013.01); *A61K 33/04* (2013.01)

(58) Field of Classification Search
USPC .................................. 514/170, 171
See application file for complete search history.

(56) References Cited

U.S. PATENT DOCUMENTS

| 4,835,147 A | * | 5/1989 | Roberts | .......... | 514/178 |
| 6,299,896 B1 | * | 10/2001 | Cooper et al. | ........ | 424/441 |
| 2004/0192598 A1 | * | 9/2004 | Kragie | ........... | 514/12 |

FOREIGN PATENT DOCUMENTS

WO    WO92/11855    *  7/1992

OTHER PUBLICATIONS

Wright, Ann. N. Y. Acad. Sci., 11057:506-524 (2005).*
Hong et al., Carcinogenesis, 2002;23(8):1297-1305.*

* cited by examiner

*Primary Examiner* — San-Ming Hui
(74) *Attorney, Agent, or Firm* — Clark A. Puntigam; Jensen & Puntigam, P.S.

(57) ABSTRACT

The basic formulation comprises a combination of three estrogens, 2-hydroxyestrone, 17-beta-estradiol and estriol, and a metabolite of an estrogen, 2-methoxyestradiol, in specified amounts. Amounts of folic acid, DHEA, testosterone, Vitamin B6, Di-Indolyl Methane, melatonin and progesterone, as well as selenium and cobalt can be added in specific amounts to the basic formulation. 2-Hydroxyestradiol, another metabolic, can also be added.

13 Claims, No Drawings

HORMONE REPLACEMENT FORMULATION

TECHNICAL FIELD

This invention relates generally to hormone replacement therapy, and more specifically concerns a new estrogen replacement formulation.

BACKGROUND OF THE INVENTION

Hormone replacement therapy has been known for some time. One particular aspect of hormone replacement therapy, known generally as estrogen replacement, has been used for over 30 years for women during or following menopause. The reason for estrogen replacement, which is usually accomplished through transdermal absorption or orally, is to make up for the decline in, or the low level of, estrogen produced by the body. Typically, estrogen production decreases and then declines dramatically during and after menopause. It is during this time period that estrogen replacement is normally prescribed by a physician. However, estrogen replacement can be prescribed in other circumstances where other causes account for a decline in estrogen production or if estrogen is produced at a lower than desirable level. This could occur in women not yet in menopause.

The reasons for estrogen replacement, which have been substantiated by scientific research over a number of years, include the prevention and/or treatment of osteoporosis and cardiovascular disease, as well as preventing age-related decline in mental function. Estrogen replacement has also been used to decrease age-related changes in appearance.

The most commonly prescribed estrogen for estrogen replacement is actually concentrated from horse urine, referred to generally as equine-conjugated estrogen or just equine estrogen. In addition, a single naturally occurring human estrogen metabolite, typically 17-beta-estradiol, in the form of a "patch", has also been and is currently prescribed. Many physicians and others have objected to equine estrogen as being inappropriate for human use and even possibly dangerous because of the fact that many individual horse estrogens are not present in human bodies and, hence, there is a lack of correlation between equine estrogen and the human estrogen which is to be replaced. There is also some evidence of the carcinogenic effect of equine estrogen.

As indicated above, the use of natural 17-beta-estradiol (a single estrogen) typically occurs in the form of an estrogen patch. While clearly more appropriate for estrogen replacement than equine estrogen, this single estrogen is believed to be incomplete for estrogen therapy, because of the large number of different estrogens and their metabolites which normally circulate in the blood stream of human bodies, particularly in women.

In this regard, several specific human estrogens, sometimes referred to as "classical" human estrogens, have been the subject of extensive research in replacement therapy. These classical estrogens include estrone, estradiol (17-beta-estradiol) and estriol. Estriol has been found to be relatively weak in its therapeutic benefits, while 17-beta-estradiol is considered the most potent, but is generally agreed to be slightly carcinogenic. Estrone also has a carcinogenic effect, although both estrone and 17-beta-estradiol are less carcinogenic than equine estrogens. There is disagreement with respect to the carcinogenic effect of estriol, ranging from non-carcinogenic or even anti-carcinogenic to slightly carcinogenic.

In an attempt to duplicate or mimic the presence of natural estrogens in the human body by replacement therapy, some physicians in the 1980s began to prescribe combinations of the three classical human estrogens, namely, a combination of estrone, 17-beta-estradiol and estriol. Typically, the combination has been 80% estriol, 10% estrone and 10% estradiol, although these percentages have varied somewhat from formulation to formulation.

However, even with natural estrogen replacement, there is still concern relative to its carcinogenic effect as well as other undesirable possibilities. Given the fact that estrogen replacement has been documented to have considerable health benefits, it is certainly desirable to develop an estrogen replacement formulation which is not only appropriate, natural and effective, but also is designed to prevent or minimize negative side effects, including carcinogenic side effects.

SUMMARY OF THE INVENTION

Accordingly, the present invention is an estrogen formulation for use in hormone replacement therapy, comprising: a combination of an amount of 2-hydroxyestrone, an amount of 17-beta-estradiol, an amount of estriol, and an amount of 2-methoxyestradiol, wherein the amounts of each ingredient are approximately as follows: wherein 2-hydroxyestrone and estriol each comprise approximately 35-45% by weight of the estrogens, wherein 17-beta-estradiol comprises approximately 10-30% by weight of the estrogens and wherein 2-methoxyestradiol comprises ½-2% of the estrogens

BEST MODE FOR CARRYING OUT THE INVENTION

As indicated above, both historically and still to a significant extent today, equine estrogen, made from horse urine, is used for human estrogen replacement therapy. However, advantages in using natural estrogen have led many physicians to prescribe a particular single naturally occurring estrogen metabolite, e.g. 17-beta-estradiol, or more recently a formulation of three "classical" estrogens, namely, estrone, 17-beta-estradiol and estriol.

Ongoing research, however, has revealed that there are many estrogens present in the human body. These additional estrogens include principally, but are not limited to, estrone, 2-hydroxyestrone, 2-methoxyestrone, 4-hydroxyestrone, 15-alpha-hydroxyestrone, 16-alphahydroxyestrone, 16-beta-hydroxyestrone, estradiol (17-beta-estradiol), 2-hydroxyestradiol, 2-methoxyestradiol, 4-hydroxyestradiol, 16-oxoestradiol, estriol, 16-epiestriol and 17-epiestriol. This is not intended to be an exhaustive list, as there are still other estrogens and their metabolites which are present in the human body. However, it does include what is presently believed to be most of the estrogens present under normal circumstances.

The present invention, in its preferred embodiment, is a new formulation involving several estrogens which are normally circulating in the human body, in combination with a number of other elements which are designed to complement and work in conjunction with the selected estrogens to enhance and increase their therapeutic effect, as well as reducing their anti-therapeutic effects/disadvantages.

The new formulation is based on estrogen levels which are more closely aligned with the way actual estrogens are present and at work in the body. The two most abundant estrogens present in the blood stream are estriol and 2-hydroxyestrone, in approximately equal amounts. 17-beta-estradiol was included in the present formulation, since it is the most therapeutically effective. 2-Hydroxyestrone has been shown to be protective against cancer, while estriol is either non-carcinogenic or perhaps even slightly anti-carcinogenic. 17-beta-estradiol has been indicated to be somewhat carcinogenic, and hence the quantity of this ingredient is severely limited. In the present formulation, for the three estrogens, 2-hydroxyestrone and the estriol are approximately in the range of 38-44% by weight, while the 17-beta-estradiol can vary between 10-20% by weight. In an embodiment which includes just 2-hydroxyestrone and 17-beta-estradiol, the formulation is 80-90% of 2-hydroxyestrone and 10-20% of 17-beta-estradiol. From the extremely large number of possible estrogen combinations, the above combinations have been discovered to be quite effective.

More particularly with respect to the three estrogen formulations, the 17-beta-estradiol, while the smallest in quantity, is generally believed to be the most potent of all the estrogens and provides the greatest therapeutic effect, but also provides the greatest carcinogenic risk. The 2-hydroxyestrone is associated with lower degrees of cancer risk, particularly in high amounts. 2-Hydroxyestrone is sometimes referred to as "good estrogen". It is, however, considered a weak estrogen, with only a mild degree of estrogen-protective activity. However, the non-carcinogenic weak estrogen can help to protect against estrogen-related cancer by occupying selected receptor sites that might otherwise be stimulated by the more carcinogenic 17-beta-estradiol. 2-Hydroxyestrone has been found to be the first or second most abundant estrogen in the human blood stream.

Estriol, while another weak estrogen, is generally regarded to be anti-carcinogenic or neutral. It also protects against carcinogenic estrogens by occupying receptor sites and is a detoxification product of the various other estrogens. Further, estriol is also either the first or second most abundant of the natural estrogens in the blood stream.

The above three estrogens, in the general quantities disclosed, are a new and therapeutically effective combination of estrogens, while minimizing any resulting cancer possibilities.

The present formulation in its preferred form includes several additional elements. One element is pyridoxine (Vitamin B6). The additional of pyridoxine is designed to help depression and fluid retention, which sometimes results from estrogen interfering with various enzyme systems which depend upon pyridoxine for proper functioning.

A second additional element is folic acid, which has often been found to be low in postmenopausal women, and has also been found to be important for maintaining normal brain function. Estrogen replacement can interfere with natural folic acid metabolism.

Another additional element is selenium, which reduces the risk of breast cancer. Lastly, cobalt has been found to be helpful, since without sufficient cobalt, the effect of estrogen replacement therapy can be significantly reduced, if not eliminated. The addition of cobalt prevents the enzymes from clearing the replacement estrogen from the body too rapidly, which helps to maintain the effectiveness of the estrogen replacement therapy regimen.

The quantities of pyridoxine and the other elements can certainly vary, as long as sufficient amounts are provided for a normal therapeutic effect. Generally, however, where the 2-hydroxyestrone and the estriol are in the range of 1000-2500 micrograms, although a preferred range is 1000-1125 micrograms, pyridoxine will be approximately 20 milligrams, with folic acid being in the range of 400-800 micrograms and selenium and cobalt in the range of 200-300 micrograms. Each of these elements ensures an effective level of the ingredients.

The above-described formulation provides not only the significant benefits of estrogen replacement in a natural form, but also includes other elements which are specifically designed to reduce or eliminate certain problems or disadvantages potentially caused by replacement estrogen, or as a side effect thereof. Hence, the present formulation is an effective but safe hormone treatment, maintaining the advantages of estrogen replacement without the previous disadvantages.

The protective effect of the above-described formulation can be improved with the addition of selected estrogenic metabolites, as well as other elements. It has been discovered that the addition of certain metabolites to the above-described formulation, not heretofore used in hormone replacement therapy, will reduce potential adverse cardiovascular and carcinogenic effects of such therapy, including specifically the above formulation. The selected metabolites are particular estrogenic metabolites of estradiol.

Estradiol itself induces various diverse biological effects in various tissues and/or organs, by a direct interaction of the estradiol with estradiol receptors (ERs) that in turn activate a specific set of genes which have specific effective and protective biological effects on those tissues and/or organs. Estradiol is also known to induce protective biological effects via ER-independent means. Estradiol is converted into various metabolites via diverse pathways, into both estrogenic and estrogenic metabolites, certain selected ones of which possess protective biological action.

The following estradiol metabolites are effective when added to the above formulation: 2-methoxyestradiol and 2-hydroxyestradiol, to produce an improved formulation. 2-Hydroxyestradiol and 2-methoxyestradiol (2-MeO) are downstream metabolites of the parent hormone, 17-beta-estradiol, which is part of the above described formulation. Estradiol is generally metabolized by oxidative metabolism to form the desired hydroxylated metabolite, 2-hydroxyestradiol. 17-Beta-estradiol is metabolized by phase 1 and 2 hepatic enzymes into 2-methoxyestradiol, which is the preferred metabolite in this improved formulation.

The above metabolites, in particular 2-methoxy-estradiol, but also 2-hydroxyestradiol, are generally regarded as safe and produce protective effects relative to cardiac health and against possible breast cancer, which are risks associated with conventional HRT therapy, as well as leukemia and multiple myeloma, among others. 2-MeO is also supportive of good kidney function, and reduces hypertension. The metabolites thus provide hormonal support while also providing protection against undesirable effects.

Generally, as women age, the liver produces less of the protective metabolites. Hence, it is advantageous to include selected metabolites with a natural combination of estrogens, such as set forth in the above formulation. The specific metabolites discussed above, 2-methoxyestradiol (as well as its sulfated metabolite) and 2-hydroxyestradiol have not heretofore been used or considered as part of a hormone replacement therapy formulation and have been selected herein from a large number of possible metabolites. The concept of including metabolites of a particular estrogen has not been heretofore proposed as part of an HRT formulation. As indicated above, 17-beta-estradiol is a potent therapeutic estrogen, but slightly carcinogenic. Use of selected metabolites of 17-beta-estradiol for protection as well as therapeutic value would therefore typically not be considered and in fact has not been heretofore so considered.

2-Methoxyestradiol is produced via an enzymatic O-methylation process, following the hydroxylation of estradiol, i.e. it is a downstream metabolite of 17-beta-estradiol. Estradiol and its hydroxylated metabolites can be further metabolized to produce sulfates, such as sulfated M-MeO, which is also an effective metabolite in HRT. In general, 2-methoxyestradiol and 2-hydroxyestradiol are the most biologically active and protective of tissues and organs, providing protection for heart and kidney function and against cancers which may be otherwise induced by hormone replacement therapy formulations, with 2-methoxyestradiol being presently the preferred metabolite.

In addition to the above-described metabolites, other elements/agents may be added to the formulation, including vitamin B6 (pyridoxine) which acts as a catalyst, and DHEA, which improves glucose tolerance, decreases body fat and increases bone mass. Women need androgens to protect against the adverse metabolic breakdown of estrogens. When DHEA is presented simultaneously with estrogens, breast cell cancer growth is inhibited. DHEA thus has a protective effect relative to breast cancer. Further, testosterone, progesterone and melatonin are desirable additional agents. Melatonin, a natural antioxidant, protects against breast cancer, and improves breast cell health. Other elements include folic acid, cobalt and selenium.

Another effective agent is Di-Indolyl Methane (DIM), which regulates the metabolism of estrogen. It tends to shunt the metabolism of estrogens toward the protective estrogens and away from the harmful estrogens. An effective amount is 60-300 milligrams.

Accordingly, a desirable hormone replacement therapy program could include a formulation of 2-hydroxyestrone, 17-beta-estradiol, estriol, and 2-MeO estrogen, as well as possibly 2-hydroxyestradiol, along with selected amounts of additional agents such as testosterone, folic acid, Di-Indolyl Methane and pyridoxine, taken in the morning (AM), while a formulation of progesterone, DHEA and melatonin could be taken in the evening. The amounts of the additional agents are: progesterone 1 mg-100 mg; testosterone ½ mg-5 mg; DHEA 1 mg-50 mg; folic acid 100 mcg-2 mg; Vitamin B6 (pyridoxine) 1 mg-100 mg; and Di-Indolyl Methane 60-300 milligrams.

A preferred basic formulation comprising the key estrogenic ingredients and their relative percentage amounts by weight is:

| | |
|---|---|
| 2-hydroxyestrone | 35-45% |
| Estriol | 35-45% |
| 17-beta-estradiol | 10-30% |
| 2 methoxyestradiol | ½-2% |
| when 2-hydroxyestradiol is added | 2-10% |

Specific amounts in a formulation include: 600-1200 micrograms of 2-hydroxyestrone, 1000-1500 micrograms of estriol, 200-500 micrograms of 17-beta-estradiol and 15-50 micrograms of 2-methoxyestradiol. 15-50 micrograms of 2-hydroxyestradiol are used when that metabolite is part of the formulation.

The formulations can be administered in various forms, using known techniques, including oral, such as in capsules or tablets, in various topical forms, in the mouth or on the skin, rectal parenteral, or vaginal. The formulations may conveniently be presented in unit dosage form or sub-doses, and prepared by conventional pharmaceutical techniques.

Although a preferred embodiment of the invention has been disclosed here for purposes of illustration, it should be understood that various changes, modifications and substitutions may be incorporated without departing from the spirit of the invention, which is defined by the claims which follow. In particular, the amounts of the various elements can be varied somewhat, as long as the therapeutic effect described is maintained.

What is claimed is:

1. A hormone replacement estrogen formulation for use in hormone replacement therapy for menopausal or post-menopausal women, comprising:
    a combination of an amount of 2-hydroxyestrone, an amount of 17-beta-estradiol, an amount of estriol, and an amount of 2-methoxyestradiol, wherein the amounts of each ingredient are approximately as follows: wherein 2-hydroxyestrone and estriol each comprise approximately 35-45% by weight of the estrogens, wherein 17-beta-estradiol comprises approximately 10-30% by weight of the estrogens and wherein 2-methoxyestradiol comprises ½-2% by weight of the estrogens, wherein the estrogens and the amounts thereof are effective for replacement of estrogens lost in menopause.

2. The formulation of claim 1, including an amount of 2-hydroxyestradiol, approximately 2-10% by weight of the estrogens.

3. The formulation of claim 1, including an amount of Vitamin B6.

4. The formulation of claim 1, including an amount of DHEA.

5. The formulation of claim 1, including an amount of Di-Indolyl Methane.

6. The formulation of claim 1, including an amount of testosterone, and an amount of melatonin.

7. The formulation of claim 6, including an amount of progesterone.

8. The formulation of claim 1, including an amount of cobalt and an amount of selenium.

9. The formulation of claim 1, wherein the formulation comprises 600-1200 micrograms of 2-hydroxyestrone, 200-500 micrograms of 17-beta-estradiol, 1000-1500 micrograms of estriol and 15-50 micrograms of 2 methoxyestradiol.

10. The formulation of claim 8, including 50-200 grams of 2-hydroxyestradiol.

11. The formulation of claim 9, including 5-25 milligrams of DHEA, 0.5-5.0 milligrams of testosterone, 0.5-5 milligrams of melatonin and 60-300 milligrams of Di-Indolyl Methane.

12. A method of hormone replacement therapy, comprising the steps of:
    Using a formulation in the morning, comprising: an amount of 17-beta-estradiol, an amount of estriol, an amount of 2-hydroxyestrone and an amount of 2-methoxyestradiol, testosterone, vitamin B6, folic acid and Di-Indolyl Methane; and using another formulation in the evening, comprising: progesterone, DHEA, and melatonin, wherein the morning formulation of 2-hydroxyestrone and estriol each comprise approximately 35-45% by weight of the estrogens, wherein 17-beta-estradiol comprises approximately 10-30% by weight of the estrogens and wherein 2-methoxyestradiol comprises ½- 2% by weight of the estrogens, wherein the estrogens and the amount thereof are effective for replacement of estrogens lost in menopause.

13. The method of claim 12, wherein the morning formulation includes an amount of 2-hydroxyestradiol 2-10% by weight of the estrogens.

\* \* \* \* \*